US010639408B2

(12) United States Patent
Rigert et al.

(10) Patent No.: US 10,639,408 B2
(45) Date of Patent: May 5, 2020

(54) BREAST SHIELD

(71) Applicant: MEDELA HOLDING AG, Baar (CH)

(72) Inventors: Mario Rigert, Buchrain (CH); Daniela Käppeli, Zug (CH); André Schlienger, Maschwanden (CH)

(73) Assignee: MEDELA HOLDING AG, Baar (CH)

( * ) Notice: Subject to any disclaimer, the term of this patent is extended or adjusted under 35 U.S.C. 154(b) by 109 days.

(21) Appl. No.: 15/550,994

(22) PCT Filed: Feb. 9, 2016

(86) PCT No.: PCT/EP2016/052728
§ 371 (c)(1),
(2) Date: Aug. 14, 2017

(87) PCT Pub. No.: WO2016/131681
PCT Pub. Date: Aug. 25, 2016

(65) Prior Publication Data
US 2018/0028733 A1 Feb. 1, 2018

(30) Foreign Application Priority Data
Feb. 20, 2015 (EP) .................................. 15155890

(51) Int. Cl.
*A61M 1/06* (2006.01)

(52) U.S. Cl.
CPC ............ *A61M 1/066* (2014.02); *A61M 1/064* (2014.02)

(58) Field of Classification Search
CPC ........ A61M 1/064; A61M 1/066; A61M 1/08; A61M 1/06; A61M 1/062; A61M 1/068; A61M 2210/1007

(Continued)

(56) References Cited

U.S. PATENT DOCUMENTS

| 4,772,262 A | 9/1988 | Grant et al. |
| 5,514,166 A * | 5/1996 | Silver ................... A61M 1/064 450/36 |

(Continued)

FOREIGN PATENT DOCUMENTS

| CN | 1466470 A | 1/2004 |
| CN | 202036597 U | 11/2011 |

(Continued)

OTHER PUBLICATIONS

International Search Report for International Application No. PCT/EP2016/052728, dated Apr. 13, 2016.

(Continued)

*Primary Examiner* — Nilay J Shah
*Assistant Examiner* — Nidah M Hussain
(74) *Attorney, Agent, or Firm* — Marshall, Gerstein & Borun LLP

(57) ABSTRACT

A breast shield for a breast pump for expressing human breast milk, comprising a funnel for applying to the human mother's breast and a connection part, wherein the funnel widens in the direction of the mother's breast and encloses at least one nipple and one areola surrounding the nipple of the mother's breast. The funnel comprises an end near to the breast, which forms a contact edge for contacting the mother's breast. The breast shield has a through-opening which extends from the end of the funnel near the breast up to the end of the connection part further from the breast, and which serves to apply a negative pressure to the mother's breast and to discharge expressed breast milk. The contact edge of the funnel is formed by a space curve that is not positioned in one plane, wherein the funnel has at least two planes of symmetry. The breast shield permits an application on the mother's breast that is optimally sealing and comfortable for the mother.

10 Claims, 4 Drawing Sheets

(58) Field of Classification Search
USPC .......................................................... 604/74
See application file for complete search history.

(56) References Cited

U.S. PATENT DOCUMENTS

| | | | |
|---|---|---|---|
| 6,383,164 B1* | 5/2002 | Johansen | A61M 1/06 604/74 |
| 6,387,072 B1 | 5/2002 | Larsson et al. | |
| 6,673,037 B1* | 1/2004 | Silver | A61M 1/066 604/74 |
| 6,723,066 B2 | 4/2004 | Larsson et al. | |
| 7,413,557 B2 | 8/2008 | Samson et al. | |
| 2005/0080351 A1 | 4/2005 | Larsson | |
| 2006/0111664 A1* | 5/2006 | Samson | A61M 1/06 604/74 |
| 2006/0116632 A1 | 6/2006 | Gillan | |
| 2015/0328380 A1 | 11/2015 | Furrer et al. | |

FOREIGN PATENT DOCUMENTS

| | | |
|---|---|---|
| CN | 202620330 U | 12/2012 |
| GB | 2138686 A | 10/1984 |
| RU | 2004123458 A | 4/2005 |
| TW | 201427730 A | 7/2014 |
| WO | WO-00/33897 A1 | 6/2000 |
| WO | WO-02/26290 A2 | 4/2002 |
| WO | WO-03066133 A1 | 8/2003 |
| WO | WO-2004/000390 A1 | 12/2003 |
| WO | WO-2011/035488 A1 | 3/2011 |

OTHER PUBLICATIONS

Taiwan Search Report for Application No. 105104734, dated Aug. 28, 2019.
Russian Search Report for Application No. 2017127967/14 (048245), dated Jul. 5, 2019.

* cited by examiner

BREAST SHIELD

CROSS-REFERENCE TO RELATED APPLICATION

The present application is the US national phase of International PCT Application No. PCT/EP2016/052728, filed Feb. 9, 2016, which claims priority to European Patent Application No. 15155890.5, filed Feb. 20, 2015. The priority application EP15155890.5, is hereby incorporated by reference.

TECHNICAL FIELD

The present invention relates to a breast shield for a breast pump for expressing human breast milk.

PRIOR ART

Breast-pump systems for expressing human breast milk are well known. They have a vacuum pump, which is operated manually or by electric motor, at least one breast shield, for bearing against the mother's breast, an adapter and a milk-collecting container, for collecting the pumped-out milk. The breast shield is connected to the vacuum pump directly or via a suction line, and therefore a cyclically varying negative pressure can be applied to the breast, in the breast shield, in order for the milk to be pumped out of the breast. The adapter retains the breast shield and connects it to the vacuum pump or the suction line. The adapter, in addition, allows connection to the milk-collecting container, either by direct coupling of the container to the adapter or via a milk line.

Known breast shields have a funnel and a connection part for connecting to an adapter. The funnels are usually designed in the form of a truncated cone, it being possible for them to be rigid or soft. Rigid funnels, in addition, may be provided with a soft insert.

The funnel should butt as far as possible with sealing action against the mother's breast, in order that an effective pumping chamber can be formed by the mother's breast and breast shield. In addition, it should bear comfortably against the mother's breast, so that pumping is as relaxed as possible and, as far as possible, does not result in pressure marks. The prior art discloses various breast shields which seek to achieve these aims.

WO 2011/035488 discloses a relatively small, very flexible breast shield, of which the opening angle adapts itself to the breast.

U.S. Pat. No. 6,673,037 discloses a rigid breast shield having a funnel which has an elliptical outline. Elevations are present on the inside of the funnel and act on the breast. U.S. Pat. No. 4,772,262 discloses a soft breast shield with an elliptical opening.

U.S. Pat. No. 7,413,557 describes a breast shield having an asymmetrical funnel which has an upper side for butting against the upper side of the breast and an underside for butting against the lower side of the breast. This breast shield has the disadvantage that it is too large for small breasts and likewise does not provide optimal abutment against specific shapes of breast. The breast shield according to GB 2 138 686 is also asymmetrical.

US 2006/0116632 proposes to arrange the connection part of the breast shield at an angle to the conical funnel.

The shape and size of the human mother's breast depends very much on the individual and correspondingly differs from individual to individual. In addition, the mother's breast is not usually perfectly conical. Therefore, in particular in respect of the rigid and semi-rigid funnels, the prior art has put up with compromise solutions or offered breast shields of different sizes.

U.S. Pat. Nos. 6,387,072 and 6,723,066 disclose, for example, a breast-shield set having a rigid base and a set of breast shields of different sizes which can be inserted into the base. The funnels of the breast shields are designed in the form of truncated cones, wherein, in one embodiment, the encircling periphery has an aperture. This breast shield can be positioned on the breast such that the aperture ends up located over a sensitive or anatomically specific shaped region of the mother's breast, and this region is therefore protected.

DESCRIPTION OF THE INVENTION

It is therefore an object of the invention to provide a breast shield which butts with the best possible sealing action against the mother's breast.

In one embodiment, the breast shield according to the invention for a breast pump for expressing human breast milk has a funnel for bearing against the human mother's breast, and also has a connection part, wherein the funnel widens in the direction of the mother's breast in order to enclose at least a nipple and an areola surrounding the nipple. The funnel has an end which is directed towards the breast and forms a lay-on edge for providing contact with the mother's breast. The breast shield has a through-passage or channel which extends from that end of the funnel which is directed towards the breast to that end of the connection part which is directed away from the breast, and which serves for applying a negative pressure to the mother's breast and for the outflow of pumped-out milk. The lay-on edge of the funnel is formed by a three-dimensional curve, which is not located in a single plane, and the funnel has at least two planes of symmetry.

As an alternative, or in addition, to the at least two planes of symmetry, the funnel is a right truncated cone. It is preferably a right truncated circular cone. It may also be, for example, a right truncated cone of elliptical cross section.

Thanks to its specific three-dimensional curve shape, the breast shield according to the invention bears optimally against the breast. The specific shape allows the breast shield to be positioned against the breast in various positions of rotation or orientations. The mother can choose the position of rotation which is optimal for her and her shape of breast. "Optimal" in this text is to be understood in the sense of giving the best possible sealing action and of being soft and providing the best possible protection.

Furthermore, the breast shield with the three-dimensional curve shape appears to be more ergonomic and feminine. This does away with any possible psychological barriers perceived by the mother, which, in turn, increases the success of pumping.

It is preferably not just the funnel, but also the lay-on edge itself, which has at least two planes of symmetry.

It has been found that the breast shield is optimally shaped if the funnel and/or the lay-on edge have/has precisely two planes of symmetry.

The funnel is preferably a right truncated cone, wherein that end of the truncated cone which is directed towards the breast forms the lay-on edge. Rendering the funnel as a right truncated circular cone prevents the situation where the nipple comes into contact with the flank of the funnel during pumping.

In preferred exemplary embodiments, a projection of the lay-on edge into a plane perpendicular to a longitudinal axis of the funnel is in the form of an ellipse. If the funnel is a right truncated circular cone and the lay-on edge, in the aforementioned projection, is an ellipse, the best possible fit for a rigid breast shield is achieved.

Instead of a continuous ellipse shape, the aforementioned projection of the lay-on edge may also be some other shape. For example, it may be any desired oval shape, i.e. a planar convex shape with or without axes of symmetry. However, it may also form other continuous shapes, for example it may be meandering and be in the form of a three-leaf or four-leaf clover or of a flower. N-cornered polygonal progressions, i.e. polygonal shapes, are likewise possible in principle, the corners preferably being rounded.

The opening angle of the funnel is preferably constant over the circumference of the latter. This means that it is merely the shape of the lay-on edge which determines the optimal position of rotation of the breast shield on the mother's breast. Contact between the nipple and the inner flank of the funnel is prevented.

The funnel and/or the lay-on edge are/is preferably rigid.

The breast shield is usually produced from a plastics material. The breast shield can be used without any further inserts, although it may also be provided with inserts. The inner surface of the funnel is preferably free of elevations and depressions. However, it is also possible to have soft, semi-hard or hard structures on the inside of the funnel, as are known from the prior art.

As an alternative, the funnel and/or the lay-on edge may be soft or semi-soft.

In preferred embodiments, the lay-on edge forms an encircling lay-on surface which allows the funnel to bear flatly against the mother's breast. The lay-on edge is thus designed in the form of a decompression edge, as a result of which the circumference of the funnel bears flatly, rather than linearly, against the mother's breast.

The lay-on edge, the funnel and connection part are preferably formed in one piece. They preferably consist of the same material. The connection part serves for connecting to an adapter, which can be connected directly or indirectly to the breast pump and the milk-collecting container. The connection part and adapter are usually two separate components. However, they may likewise be formed together in one piece.

In preferred embodiments, the funnel, on its outside, has at least one haptic element, which differs from the rest of the outer surface of the funnel. These haptic elements, in a preferred embodiment, are continuous grooves or elevations which run around the funnel. The projection thereof into a plane perpendicular to the longitudinal axis of the funnel is preferably identical to the projection of the three-dimensional curve; in particular it is preferably elliptical. Thanks to said haptic elements, the mother will intuitively hold the device by the funnel. If they correspond, in addition, to the three-dimensional curve, or point towards the same, they serve as an orientation aid for the mother.

Further embodiments are specified in the dependent claims.

BRIEF DESCRIPTION OF THE DRAWINGS

Preferred embodiments of the invention will be described hereinbelow with reference to the drawings, which serve merely for explanatory purposes and should not be interpreted as being limiting in any way. In the drawings.

DESCRIPTION OF PREFERRED EMBODIMENTS

Figure 1:
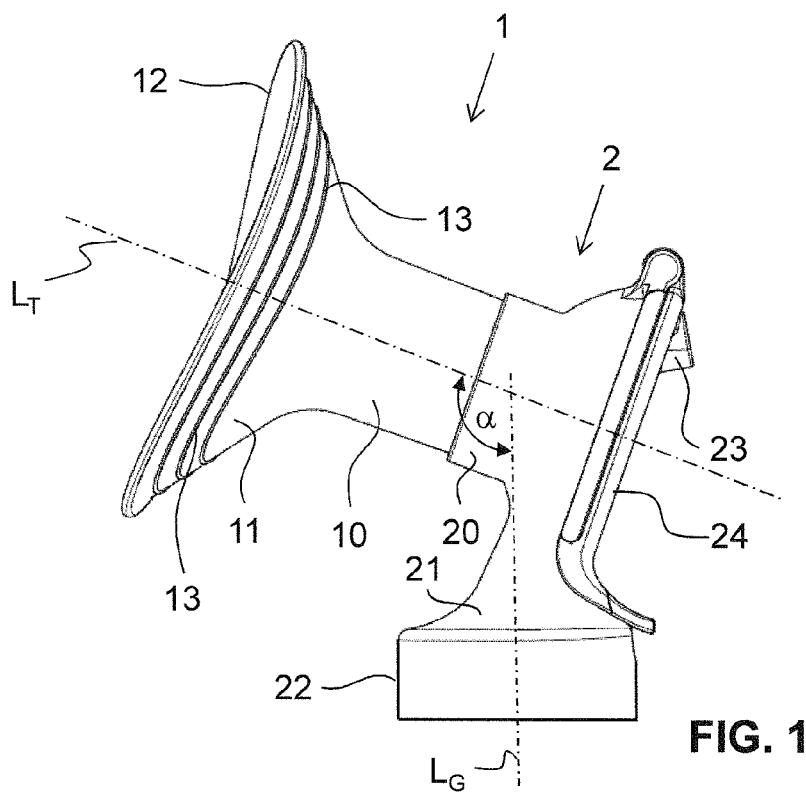
FIG. 1 shows a side view of a first embodiment of a breast shield according to the invention with an adapter.

FIGS. 1 to 10 illustrate a first embodiment of the breast shield 1 according to the invention with an adapter 2. The breast shield has a connection part 10, in this case in the form of a cylindrical connector 10, and a funnel 11, which is formed on the connector in one piece. The breast shield 1 is preferably produced from plastics material. It is preferably of a rigid design.

The breast shield 1 is retained in an accommodating part 20 of the adapter 2 by way of the connection part 10. The accommodating part 20 here is in the form of a tubular socket, into which the connection part 10 of the breast shield 1 can be plugged.

The adapter 2 has a neck 21 with a milk connection 22. The milk connection 22, in turn, is a tube portion with an internal thread 25 for fastening onto a milk-collecting container, in particular onto a neck of a milk bottle.

The longitudinal centre axis $L_T$ of the funnel 11 is preferably oriented at an angle to the longitudinal centre axis $L_G$ of the internal thread 25, and thus of the milk connection 22. The angle of inclination a is preferably 90° to 120°.

A vacuum connection 23 for a vacuum hose for connecting to a vacuum pump is present on that side of the adapter 2 which is directed away from the breast shield 1. As an alternative, the vacuum pump can be arranged directly on said connection. In addition, instead of a pump which is operated by electric motor, it is also possible for a hand-operated pump to be used with the breast shield according to the invention.

The rear side of the adapter 2, i.e. the side directed away from the breast, is closed by a cover 24 in this example.

Figure 2:
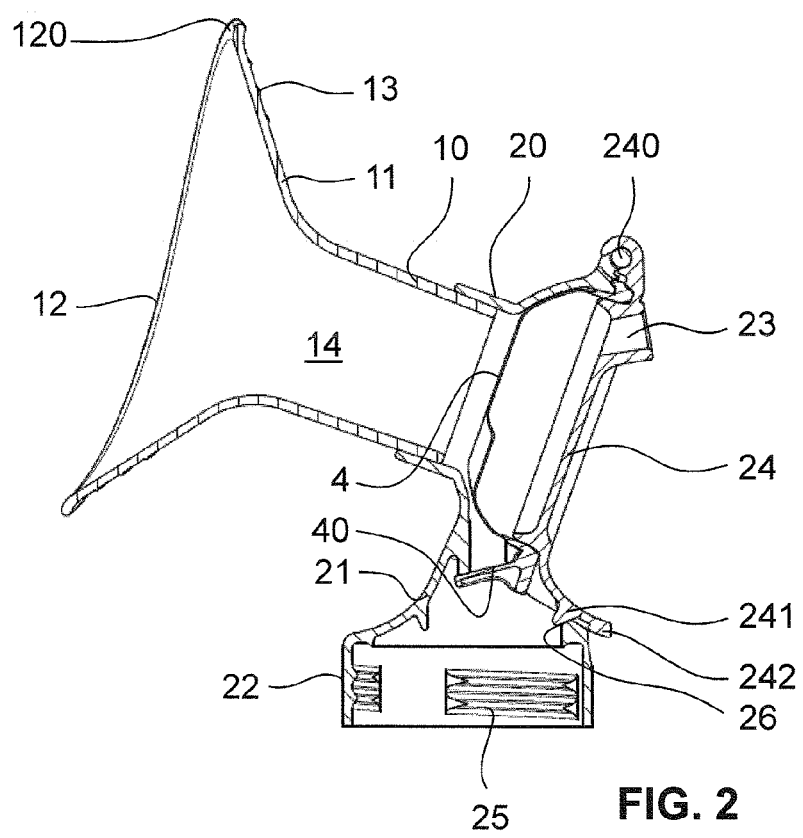
FIG. 2 shows a longitudinal section through the device according to FIG. 1.
Figure 3:
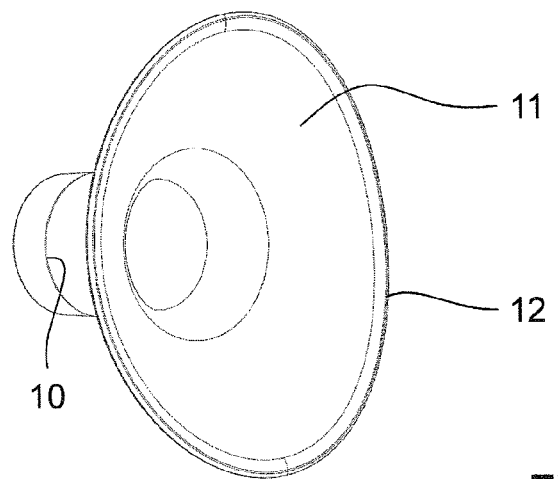
FIG. 3 shows a perspective illustration of the breast shield according to FIG. 1 as seen from the side directed towards the breast.
Figure 4:
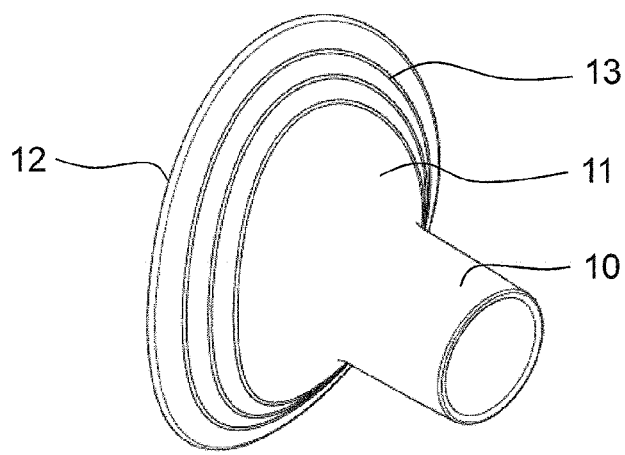
FIG. 4 shows a perspective illustration of the breast shield according to FIG. 1 as seen from the side directed away from the breast.

It can be seen in FIG. 2 that the adapter 2 contains a media-separating membrane 4, which prevents the passage of pumped-out milk from the breast to the vacuum connection 23. This prevents the vacuum pump from becoming contaminated. The media-separating membrane 4 is of flexible design and the negative or positive pressure which is applied cyclically via the suction connection 23 is transmitted thereby into the funnel 11 of the breast shield.

A lip which acts as a valve flap 40 of a non-return valve is formed on the media-separating membrane 4. The seat of the valve is formed by the adapter 2. The valve breaks the connection between a through-passage 14 of the breast shield 1 and the milk connection 22, and therefore the connection between the breast and the milk-collecting container is interrupted cyclically. This limits the dead volume in the adapter 2 as the negative pressure is being applied.

The media-separating membrane 4 can be straightforwardly mounted and, for the purpose of cleaning and/or exchange, removed. The interior of the adapter 2 is readily accessible by way of the cover 24. The cover 24, in this embodiment, is retained in a pivotable manner. 240 designates the hinge of the cover, and 241 designates a restraining nose 241, which engages in a restraining edge 26 of the rest of the adapter 2. The cover 24 is lengthened by way of a projecting handle 242, which allows it to be easily raised.

This media-separating membrane 4 and this adapter 2 are inventions which are described in a patent application by the same applicant filed on the same date as the present patent application. The patent application is entitled "Adapter with media-separating membrane for a breast shield". The content of said patent application is hereby included in this text by way of reference.

Instead of this adapter, it is also possible for another adapter, or an adapter which is connected in one piece to the breast shield, to be used with the breast shield according to the invention.

FIGS. 3 to 9 illustrate the first exemplary embodiment of the breast shield according to the invention in a number of views, some of them in perspective. The funnel 11 is designed in the form of a truncated circular cone. It has an opening angle γ which is constant over its circumference. The opening angle also remains preferably constant over the axial length of the funnel 11. In other embodiments, however, it alters over the axial length.

The funnel 11 widens in the direction of the breast. Its widened end, which is directed away from the connection part and thus is directed towards the mother's breast, forms a lay-on edge 12 for bearing against the breast. The lay-on edge 12 is of flat design, as can be seen to good effect in FIGS. 1 and 2. This lay-on surface 120 means that the funnel 11 bears flatly, rather than just linearly, against the breast.

Figure 10:
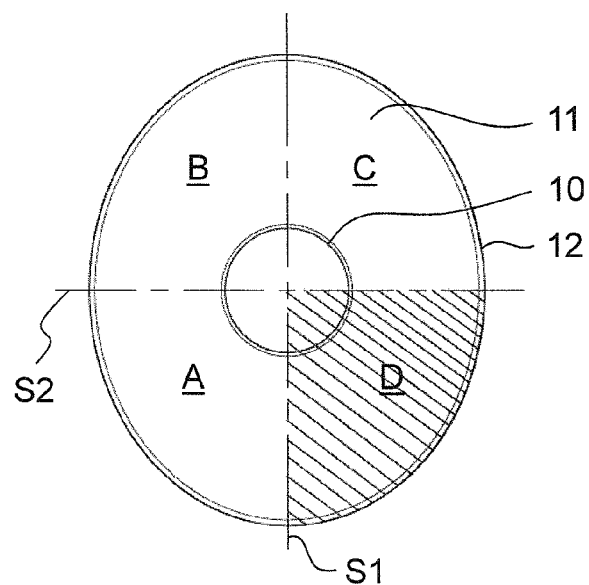
FIG. 10 shows a view of the breast shield with additionally depicted auxiliary lines and planes of symmetry.
Figure 5:
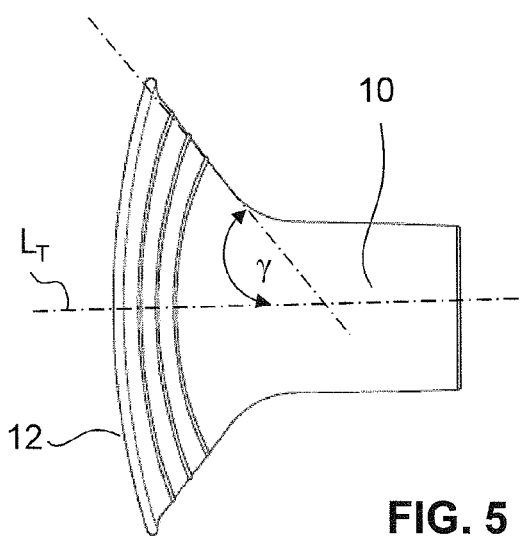
FIG. 5 shows a first side view of the breast shield according to FIG. 1.
Figure 6:
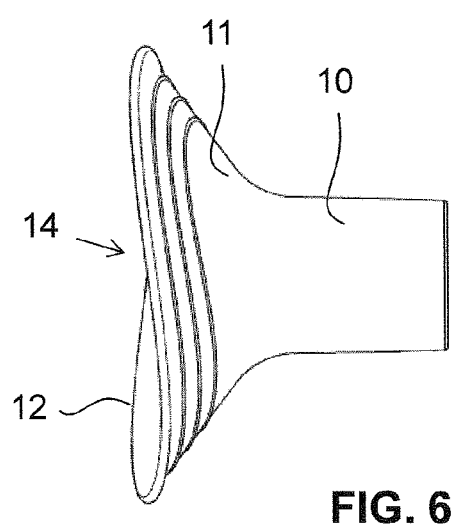
FIG. 6 shows a second side view of the breast shield according to FIG. 1.
Figure 7:
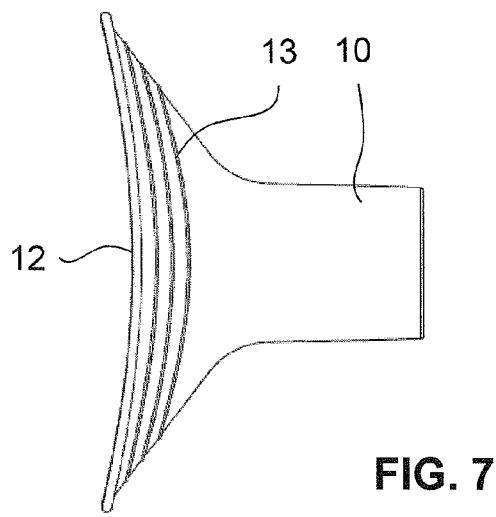
FIG. 7 shows a third side view of the breast shield according to FIG. 1.
Figure 8:
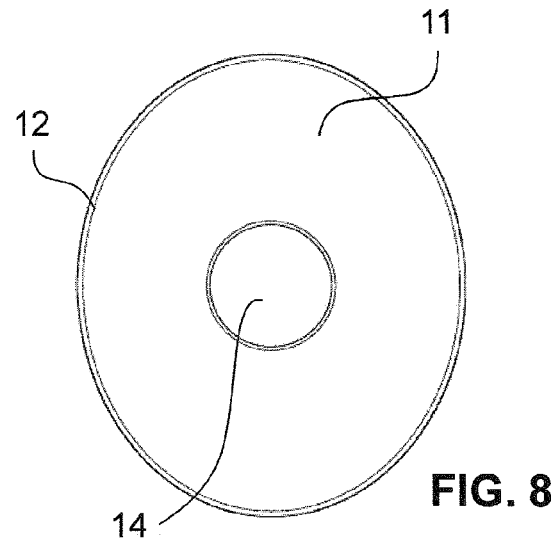
FIG. 8 shows a view of the breast shield according to FIG. 1 on the side directed towards the breast.

The lay-on edge 12 is a three-dimensional curve, i.e. it is not located in a single plane. The three-dimensional arrangement of the lay-on edge 12 can be seen to good effect by comparing FIGS. 5 to 7. As seen geometrically, the truncated circular cone, rather than being cut in a single plane, is cut three-dimensionally. Suitable selection of the cutting curve gives rise, as illustrated here, to a lay-on edge 12 of which the projection into a plane perpendicular to the longitudinal centre axis $L_T$ of the funnel 11 corresponds to an ellipse. This can be seen to good effect in FIGS. 8 and 9. As is illustrated in FIG. 10, this projection has two symmetries. Its surface area can be divided up into four equal-sized zones A, B, C, D which are mirror-symmetrical to one another in relation to the axes of symmetry $S_1$ and $S_2$. These two axes of symmetry $S_1$ and $S_2$, in addition, are part of the two planes of symmetry, which run perpendicularly to the surface of the sheets of drawings. They form the two planes of symmetry of the funnel 11 and the lay-on surface 12. These are preferably the only two planes of symmetry. They are designated here likewise by $S_1$ and $S_2$.

Figure 9:
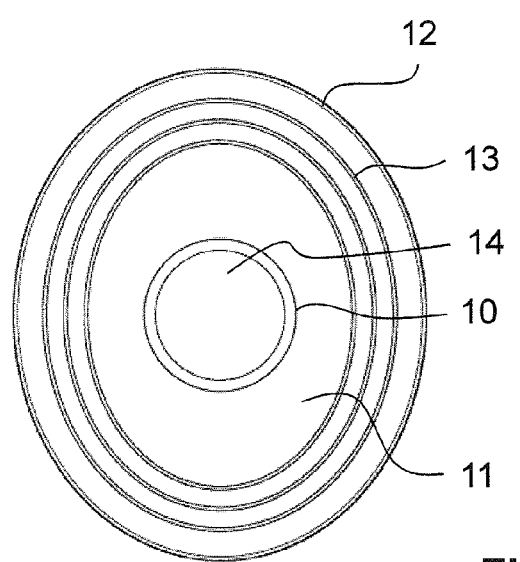
FIG. 9 shows a view of the breast shield according to FIG. 1 on the side directed away from the breast.
Figure 11:
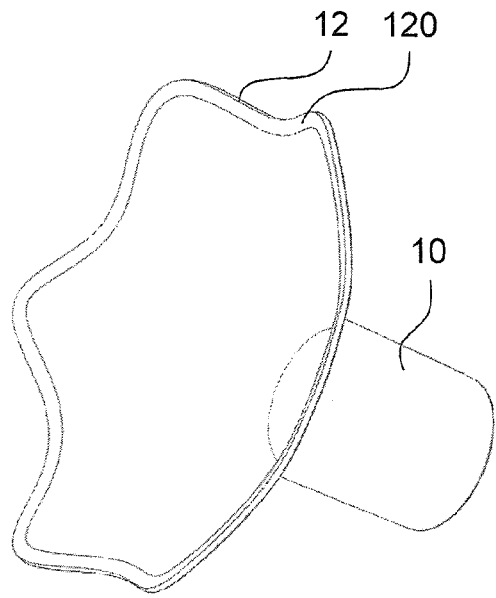
FIG. 11 shows a perspective illustration of a second embodiment of a breast shield according to the invention as seen from the side directed towards the breast.
Figure 12:
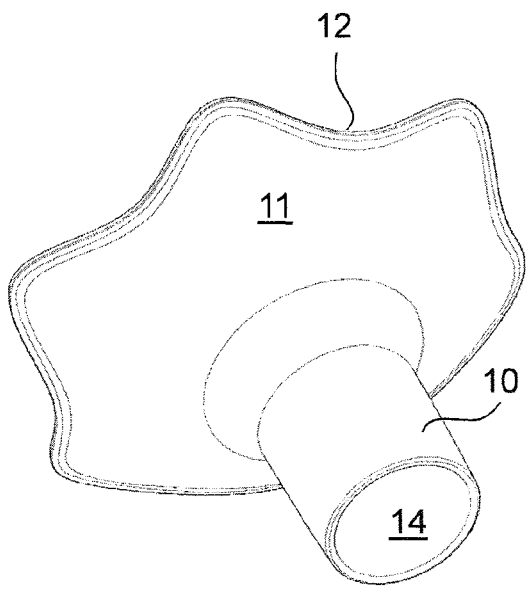
FIG. 12 shows a perspective illustration of a second embodiment of the breast shield according to FIG. 11 as seen from the side directed away from the breast.
Figure 13:
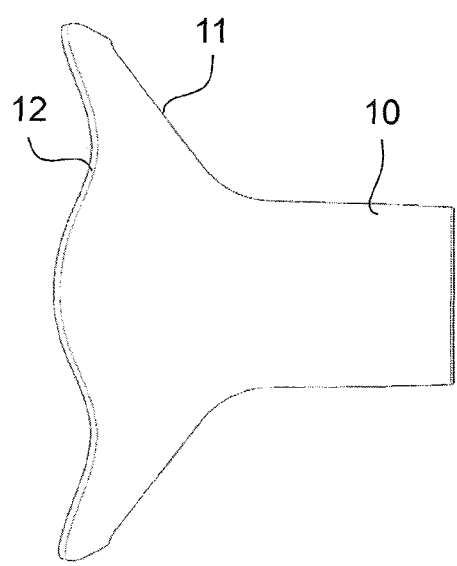
FIG. 13 shows a side view of the breast shield according to FIG. 11.
Figure 14:
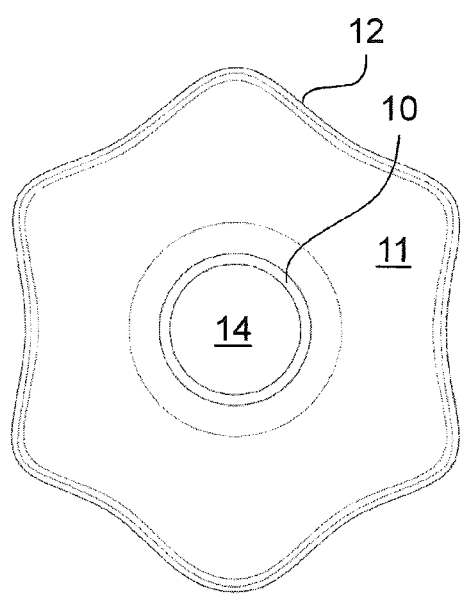
FIG. 14 shows a view of the breast shield according to FIG. 11 on the side directed away from the breast.

The essentially smooth, outer surface of the funnel 11 is provided with continuous, encircling ribs 13. The ribs 13 are spaced apart from one another and are preferably the same shape as the lay-on edge 12. As can be seen in FIG. 9, they have an elliptical outline.

FIGS. 11 to 14 illustrate a further exemplary embodiment of the breast shield according to the invention. It is the same shape as the breast shield which has already been described. The lay-on edge 12 is likewise a three-dimensional curve, as described above. However, it is of a meandering or an undulating design. It, or its projection, has a flower-like shape in this example.

The breast shield according to the invention can butt against the mother's breast in a manner which provides optimal sealing and is comfortable for the mother.

What is claimed is:

1. A breast shield for a breast pump for expressing human breast milk, wherein the breast shield has a funnel for bearing against a human mother's breast, and also has a connection part, wherein the funnel widens in a direction of the mother's breast in order to enclose at least a nipple and an areola surrounding the nipple, wherein the funnel has an end which is directed towards the mother's breast, and forms a lay-on edge for providing contact with the mother's breast, and wherein the breast shield has a through-passage which extends from the end of the funnel which is directed towards the mother's breast to an end of the connection part which is directed away from the mother's breast, and which serves for applying a negative pressure to the mother's breast and for an outflow of pumped-out breast milk, wherein the lay-on edge of the funnel is formed by a three-dimensional curve, which is not located in a single plane, and wherein the funnel has precisely two planes of symmetry, wherein the lay-on edge has precisely two planes of symmetry and wherein an opening angle of the funnel is constant over the circumference of the funnel, wherein the funnel is a truncated right cone, and wherein an end of the truncated right cone which is directed towards the mother's breast forms the lay-on edge.

2. The breast shield according to claim 1, wherein a projection of the lay-on edge into a plane perpendicular to a longitudinal axis of the funnel is an ellipse.

3. The breast shield according to claim 1, wherein a projection of the lay-on edge into a plane perpendicular to a longitudinal axis of the funnel is a continuous meandering curve.

4. The breast shield according to claim 1, wherein the funnel is rigid.

5. The breast shield according to claim 1, wherein the lay-on edge forms an encircling lay-on surface which allows the funnel to bear flatly against the mother's breast.

6. The breast according to claim 1, wherein the lay-on edge is rigid.

7. The breast shield according to claim 1, wherein the funnel and the connection part are formed in one piece.

8. The breast shield according to claim 1, wherein the funnel, on its outer surface, has at least one haptic element, which differs from the rest of the outer surface of the funnel.

9. A breast shield for a breast pump for expressing human breast milk, wherein the breast shield has a funnel for bearing against a human mother's breast, and also has a connection part, wherein the funnel widens in a direction of the mother's breast and encloses at least a nipple and an areola surrounding the nipple, wherein the funnel has an end which is directed towards the mother's breast and forms a lay-on edge for providing contact with the mother's breast, and wherein the breast shield has a through-passage which extends from the end of the funnel which is directed towards the mother's breast to an end of the connection part which is directed away from the mother's breast, and which serves for applying a negative pressure to the mother's breast and for an outflow of pumped-out breast milk, wherein the funnel is a truncated right cone, and wherein the lay-on edge of the funnel is formed by a three-dimensional curve, which is not located in a single plane and wherein a projection of the lay-on edge into a plane perpendicular to a longitudinal centre axis of the funnel is an ellipse.

10. A breast shield for a breast pump for expressing human breast milk, wherein the breast shield has a funnel for bearing against a human mother's breast, and also has a connection part, wherein the funnel widens in a direction of the mother's breast in order to enclose at least a nipple and an areola surrounding the nipple, wherein the funnel has an end which is directed towards the mother's breast, and forms a lay-on edge for providing contact with the mother's breast, and wherein the breast shield has a through-passage which extends from the end of the funnel which is directed towards the mother's breast to an end of the connection part which is directed away from the mother's breast, and which serves for applying a negative pressure to the mother's breast and for an outflow of pumped-out breast milk, wherein the lay-on edge of the funnel is formed by a three-dimensional curve, which is not located in a single plane, wherein the funnel and the lay-on edge have at least two planes of symmetry, and wherein the funnel is a truncated right cone, and wherein an end of the truncated right cone which is directed towards the mother's breast forms the lay-on edge.

* * * * *